United States Patent [19]
Leib et al.

[11] Patent Number: 5,221,977
[45] Date of Patent: Jun. 22, 1993

[54] LASER RADIATION PROTECTION SYSTEM

[75] Inventors: Kenneth G. Leib, Wantagh; Benjamin J. Pernick, Forest Hills, both of N.Y.

[73] Assignee: Grumman Aerospace Corporation, Bethpage, N.Y.

[21] Appl. No.: 841,100

[22] Filed: Feb. 25, 1992

[51] Int. Cl.⁵ .......................... G02B 5/32; G03H 1/04
[52] U.S. Cl. ...................................... 359/15; 359/19; 359/614
[58] Field of Search .................. 359/15, 19, 22, 24, 359/613, 614

[56] References Cited

U.S. PATENT DOCUMENTS

| | | | |
|---|---|---|---|
| 3,940,204 | 2/1976 | Withrington | 359/19 |
| 4,054,356 | 10/1977 | Noguchi | 359/19 |
| 4,355,858 | 10/1982 | Funato et al. | 359/19 |
| 4,601,533 | 7/1986 | Moss | 359/24 |
| 4,637,678 | 1/1987 | Moss et al. | 359/15 |
| 4,786,125 | 11/1988 | Magarinos et al. | 359/15 |
| 4,802,719 | 2/1989 | Magarinos et al. | 359/15 |
| 4,830,441 | 5/1989 | Chang | 359/24 |
| 4,978,182 | 12/1990 | Tedesco | 359/19 |
| 5,103,323 | 4/1992 | Magarinos et al. | 359/24 |

OTHER PUBLICATIONS

L. N. Itseleva, "Light Goggles Employing Liquid Crystals," Sov. J. Opt. Technol. 57 (1) Jan. 1990 pp. 32-34.
R. Weiss, "From Armaments to Eyes at Army Materials Lab," Lasers & Optronics, Nov. 1990, p. 25.

*Primary Examiner*—Martin Lerner
*Attorney, Agent, or Firm*—Pollock, VandeSande & Priddy

[57] ABSTRACT

A viewing window is equipped with a selective attenuator for a harmful incoming laser beam. The attenuator principally employs a holographic optical element which selectively deflects the laser beam where it may be absorbed or further deflected. Ordinary light passes undeflected so that it may be processed by optical equipment or a viewer.

3 Claims, 4 Drawing Sheets

LASER RADIATION PROTECTION SYSTEM

FIELD OF THE INVENTION

The present invention relates to protection systems against laser radiation, and more particularly to such a system employing a holographic optical element.

BACKGROUND OF THE INVENTION

The purpose of this invention is to protect personnel from the threat of eye damage or blindness when irradiated with a laser beam of sufficiently high power by an adversary. Similarly, this invention provides a means to protect optical components, such as TV cameras and detectors, from laser-induced damage.

In situations when the potential laser threat is known beforehand (i.e., wavelength, direction of propagation, pulsed or CW, power and energy level), various means to protect personnel or equipment are available. Such protective apparatus would, for example, consist of neutral density filters, narrow band wavelength filters, individual wavelength selective absorption filters, mechanical shutters and combinations of these items. The protective apparatus would be designed for a particular, known threat. Some of these techniques have their concomitant disadvantages such as time to respond or broad wavelength band insertion loss, inhibiting normal visual use.

For these reasons, the above-mentioned means are not entirely practical nor effective in providing the needed safety. The wavelength, pulsed or CW, of an irradiating laser source may be an unknown factor to contend with in the same way that unknown radar threats are encountered. A basic requirement of any protective system in a threatening situation is that the observer (human, camera, or detector), be able to see the surroundings with minimal visual loss (attenuation or distortion) while being protected from laser damage.

BRIEF DESCRIPTION OF THE PRESENT INVENTION

The invention described herein will satisfy the joint need for safety and visibility. The operation of its key element is based on certain holographic principles. The basic idea is to utilize a special type of holographic optical element (HOE) to remove offending laser light from the entrance aperture of an optical system with very high efficiency. This is to be accomplished at several wavelengths for which powerful lasers are known to exist in the threat environment. The ability to prevent laser light from entering the optical aperture is wavelength specific. Light from the environment at other wavelengths would not be obscured and hence observed by the viewer.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1A:
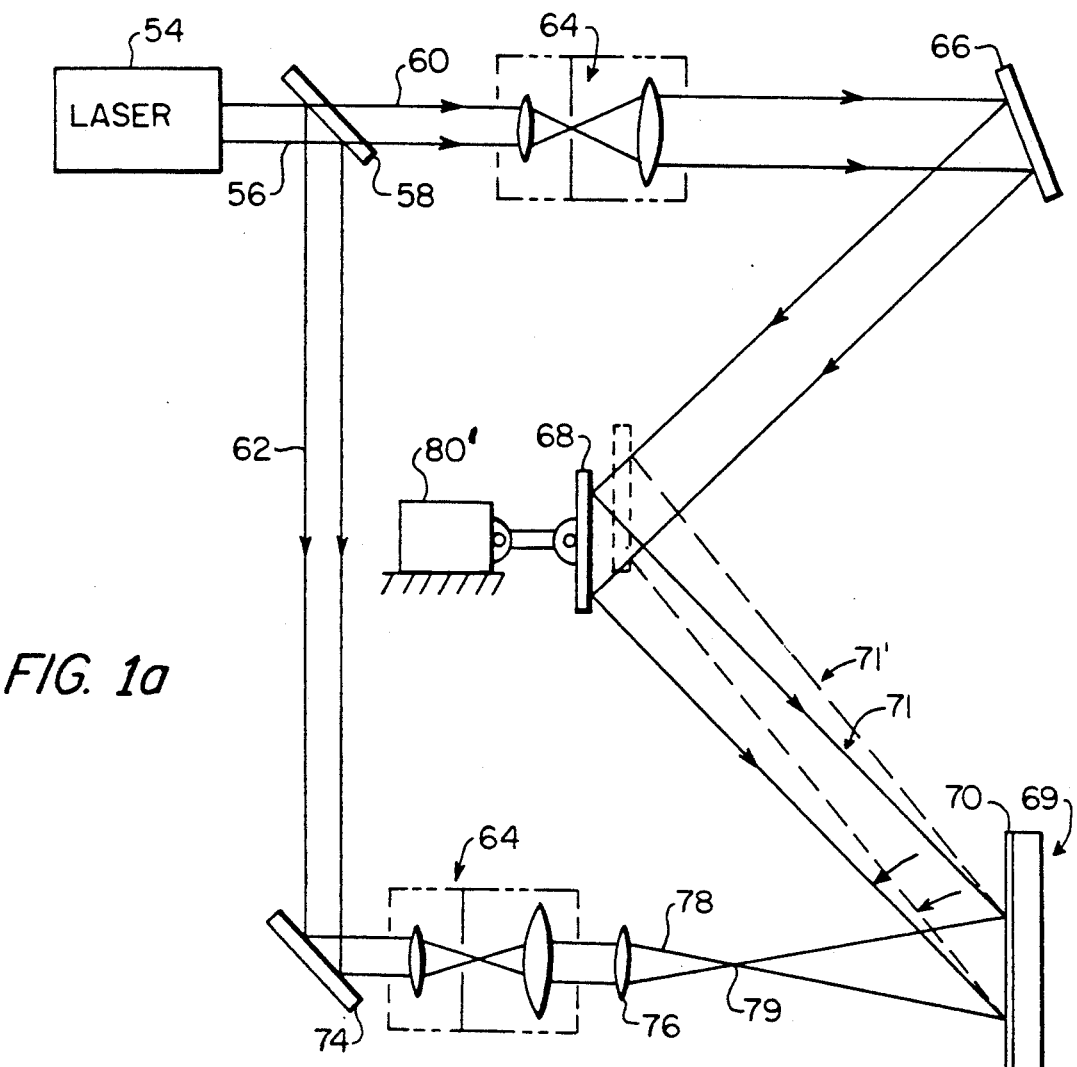
FIG. 1a is a schematic diagram illustrating the manufacture of a transmissive holographic optical element.

FIG. 1a illustrates a particular way to fabricate an HOE. In this illustration, a collimated beam of light 56 from laser 54 and a spherical wavefront from an equivalent point source 79 simultaneously expose a light sensitive material 70 on a support backing 72, the latter two constituting a hologram plate 69. This exposure forms a recording of the interference fringe pattern of these coherent beams in the material 70. A beam splitter 58 is used to form the two collimated beams, 60 and 62. Beam 60 is sent through an optical assembly 64 comprising a beam expander, pinhole filter, and collimation lens. It is then reflected from mirrors 66 and 68 such that the beam 71 is incident on the hologram plate 69. The mirror 68 can be moved via a reciprocating drive device 80' for creating multiple exposures. Beam 71 is usually called the reference beam. The second beam 62 is reflected from mirror 74 and is subsequently enlarged by means of the optical assembly 64. This beam passes through a high quality lens 76 converges as indicated at 78 and forms a focused beam spot 79. The expanding spherical wave from 79 which is called the object or signal beam exposes the film plate 69 simultaneous with beam 71. This setup is used to produce a transmissive HOE. Note that the plate 69 can be oriented normal to the reference beam 71. This is a preferred orientation for this invention.

Figure 1B:
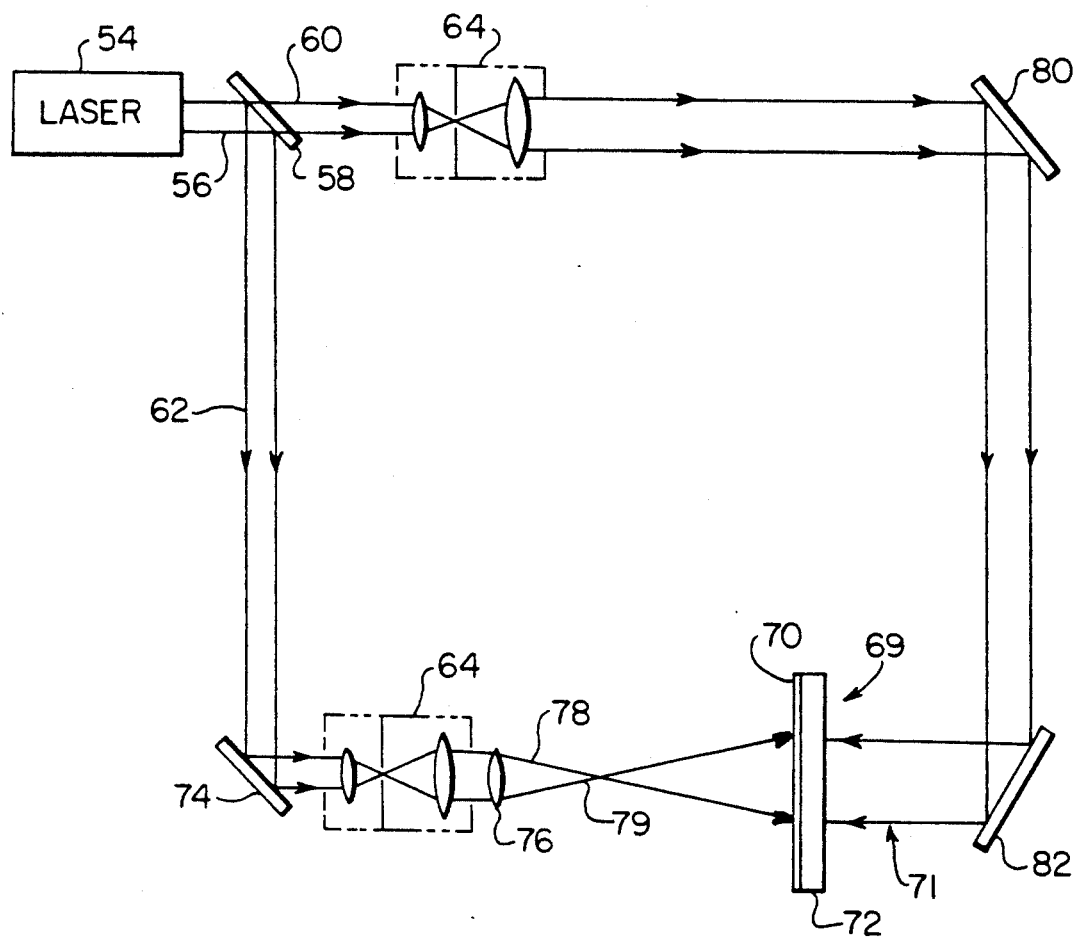
FIG. 1b is a schematic diagram illustrating the manufacture of a reflective holographic optical element.

The previous discussion pertaining to FIG. 1a produces a transmissive HOE, i.e., the unwanted laser beam referred to earlier is transmitted through the HOE and is diverted from the optical axis. However, in a second embodiment of the present invention, it is possible to make a reflective HOE. This is more clearly shown in FIG. 1b wherein comparable components are indicated by the same reference numerals as employed in FIG. 1a. As will be appreciated by viewing the figure, the reference beam 71 is projected onto the back of the hologram plate 69 by virtue of corner mirrors 80 and 82 thereby forming interference planes approximately parallel to the recording medium 70. Coaxially opposing the reference beam 71 is the expanding spherical wave from object beam 79 which impinges on the hologram plate from an opposite direction. It should be noted that the emulsion 70 may be positioned against either planar surface of the transparent support backing 72.

Figure 2:
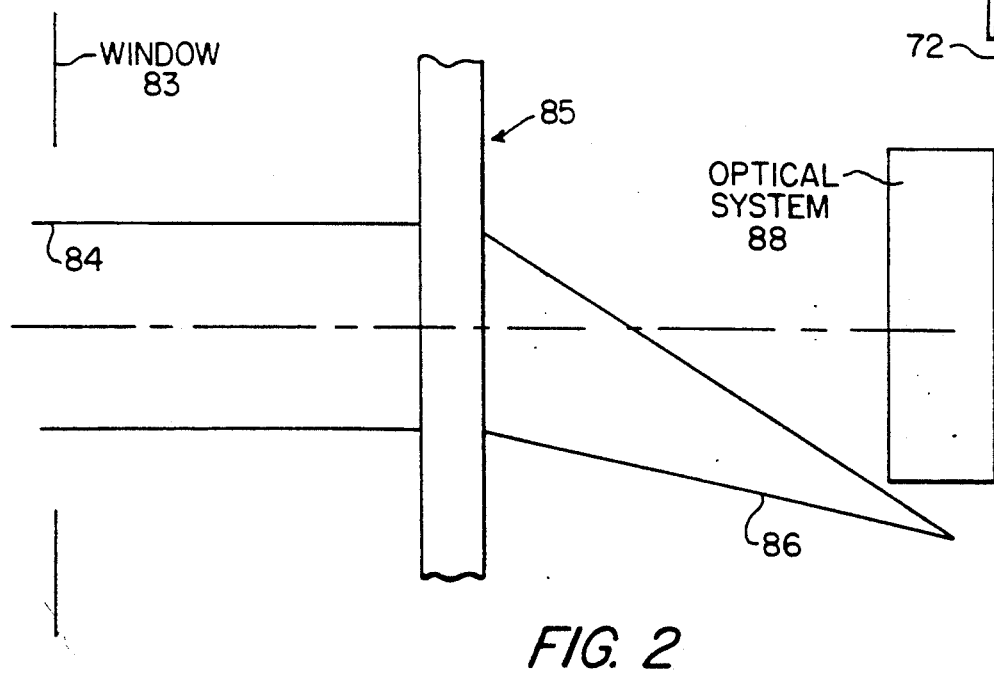
FIG. 2 is a schematic illustration of light diffraction through a holographic optical element.

Referring to FIG. 2, when the finished HOE 85 is irradiated with a laser beam 84 (outside window 83) at the same wavelength used in its manufacture and at the same angle as the reference beam in recording (FIG. 1a), the laser light transmitted by the HOE will be deflected and focused off to one side 86. This deflected beam would be blocked, absorbed, or removed from entering the optical system 88 by known means. If the HOE is a reflective type, the deflected beam will be reflected by the HOE on the opposite side to that shown in FIG. 2 and also not enter the optical system. Light at other wavelengths arriving at the same angle of incidence will be acted upon in a similar manner but with a different deflection angle. Thus, the inventive system in effect selectively attenuates incoming light by redirecting selected wavelengths for which it is designed.

Figure 6:
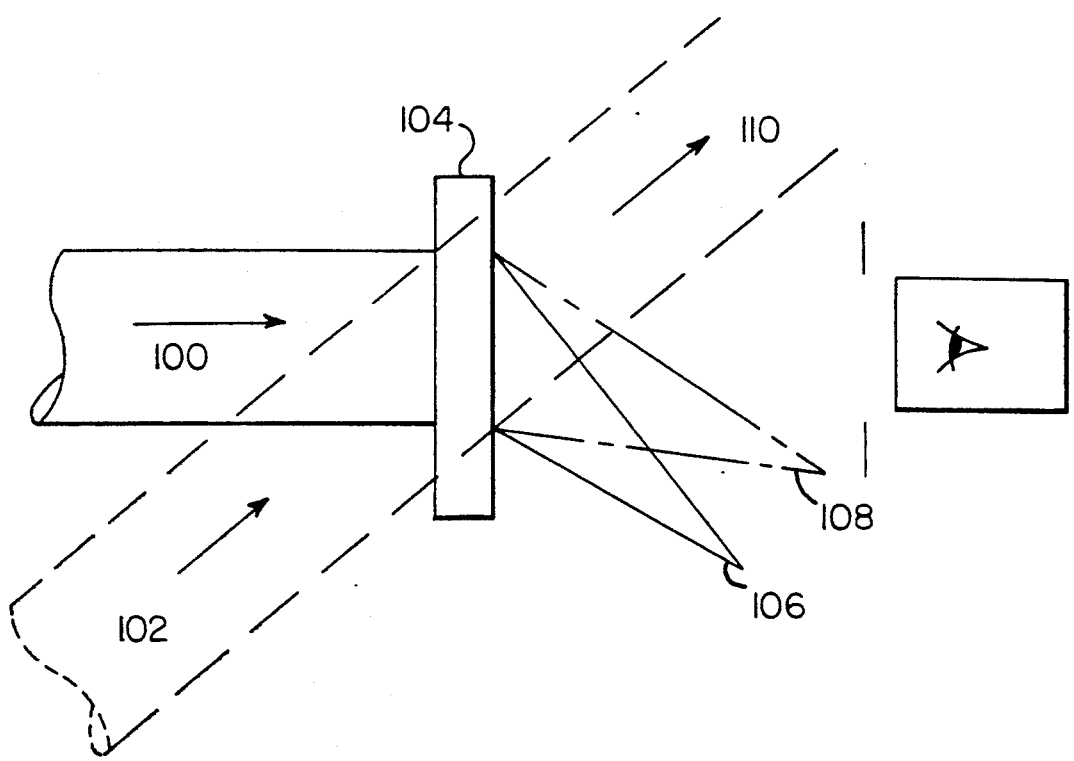
FIG. 6 is a schematic illustration indicating the deflection of a harmful laser beam for two incident beams of different incident angles.

Furthermore, with the appropriately designed HOE as described below, if laser light impinges upon the HOE at other than the small spread of design angles, the focused component of the laser beam will ideally not be transmitted by the transmissive HOE. The undeflected, so-called dc component, will be transmitted by the HOE in this case. To prevent the dc component from entering the observer optics, the incidence angle sensitivity would be designed to efficiently deflect the incident beam over a predetermined angle range. For beams entering at larger incident angles, the transmitted dc beam would exit the HOE at a sufficiently large angle so that it, too, could be blocked or bypass the entrance aperture of the observer optics. FIG. 6 shows two incident beams 100, 102 and an HOE 104. The focused beam 106 from 100 is deflected out of the way. The extreme beam 102 is also focused 108 and is the limiting angle determined by the observer entrance aperture. For larger incidence angles, the transmitted dc beam 110 does not enter the observer optics. A further implementation of this invention is to sandwich a transmissive and reflective HOE, thus distributing the power to be blocked. The transmission property of this type of HOE can be a very sensitive function of the incident angle. Thus, the ability (a) to block laser light over a wide incident angle range, (b) to efficiently deflect "out of harm's way" laser light that would be transmitted at the appropriate incidence angle, and (c) to permit observation at the ambient light environment are the basic attributes of this invention subject to the appropriate employment of the design parameters.

One of the HOE parameters that determines its performance is the separation of recorded interference fringes in the material. The fringe-to-fringe distance or separation varies with and depends upon the angle between the reference beam and the object beam upon recording. As the angle between collimated beams increases, the fringe separation approaches an asymptotic value. This value is dependent upon the beam angle orientation with respect to a normal to the recording emulsion surface. If relatively large beam angles are to be used, fringe separation will be of the order of a micron.

Figure 3:
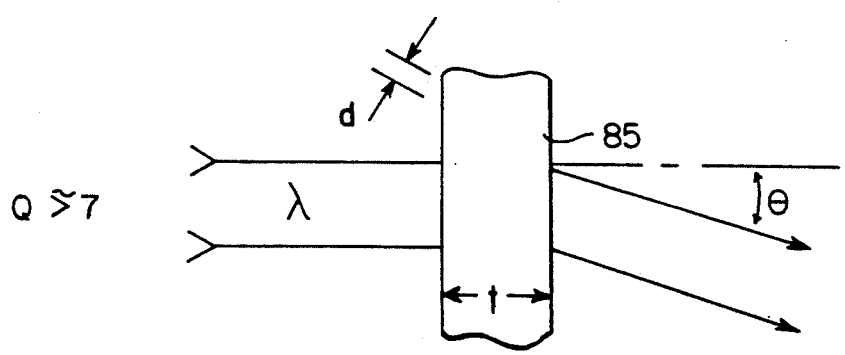
FIG. 3 is a schematic illustration of parameters for calculating a Q factor of performance for a holographic optical element.

Two other factors that influence the HOE performance are the thickness t and refractive index $n_o$ of the emulsion layer 70 at wavelength $\lambda$. With an increasing thickness for a given fringe separation d, the emerging, diffracted beam becomes highly directly. The so-called Q-factor $$Q = \frac{2\Pi\lambda t}{n_o d^2}$$

is a figure of merit which designates a mode of operation of an HOE. Thus, for example, the thicker the emulsion the narrower the acceptance angle becomes. In the illustration of FIG. 3, the HOE 85 exhibits a so-called Bragg effect for $Q > \sim 7$. In this case, the diffracted light exits in effect within a narrow neighborhood at the indicated diffraction angle $\sigma$. The focusing action of the transmitted rays of the HOE 85 are not shown in the figure. In addition, the diffraction efficiency of this type of HOE can be very high. Thus, the laser light would be completely diffracted from the in-line transmission path. Experiments have shown that, for this situation, the emulsion recording thickness is approximately 10 microns or greater.

Figure 4A:
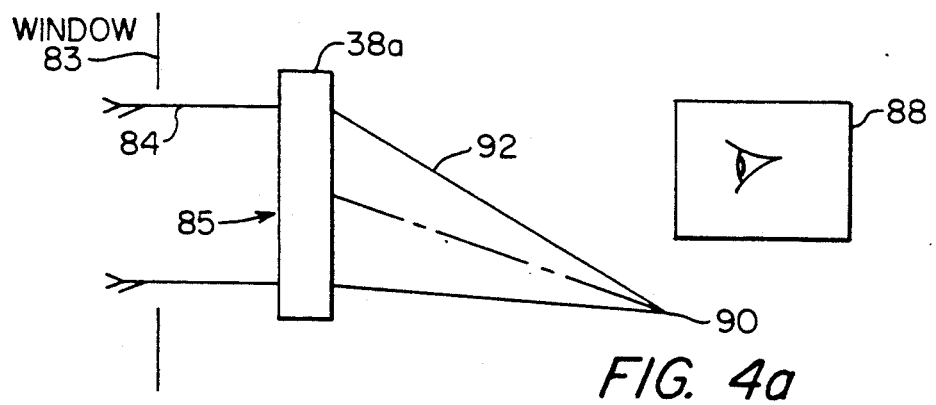
FIG. 4a is a schematic illustration indicating the diffraction of laser light away from in-line positioned optical equipment or an observer.
Figure 4B:
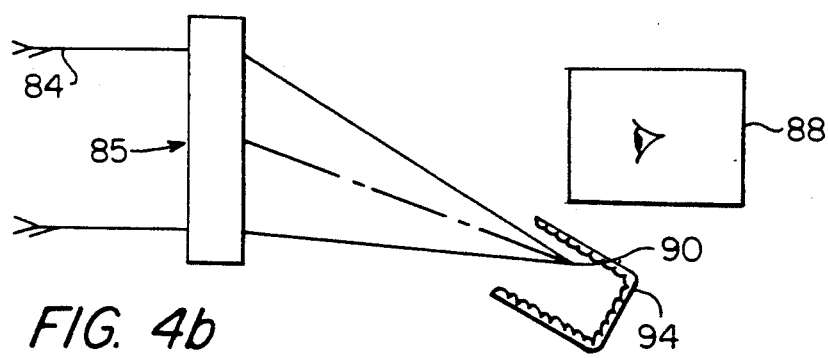
FIG. 4b is a view similar to that of FIG. 4a with an absorption medium for diffracted laser light.
Figure 4C:
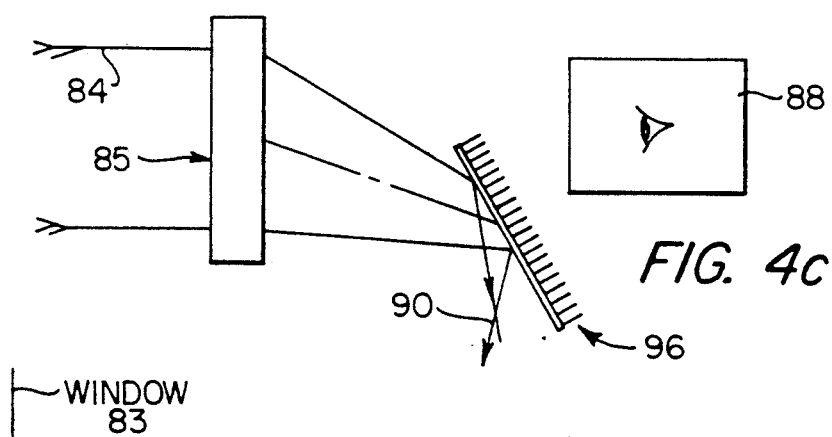
FIG. 4c is a view similar to that of FIG. 4a with a mirror or light baffle interposed in the path of laser light diffraction for further reflecting or shielding in-line optical equipment or an observer.

FIGS. 4a–4c illustrate how the laser light would be selectively deviated and prevented from entering the entrance aperture of the optical system to be protected. In FIGS. 4a–4c laser beam 84 is focused at 90 by a transmissive HOE 85. This focused beam is prevented from entering the optical system 88 by any one of several means. For example, FIG. 4a shows the laser beam deflected through an angle sufficiently large so that the focused beam 92 passes safely beyond the optical system 88. Alternately, as shown in FIGS. 4b and 4c, an absorber 94, an element 96 such as a mirror or baffle could be used to remove the laser beam from the system. In all cases, remaining light from the scene in the field of view is passed on to the optical system 88.

Figure 5:
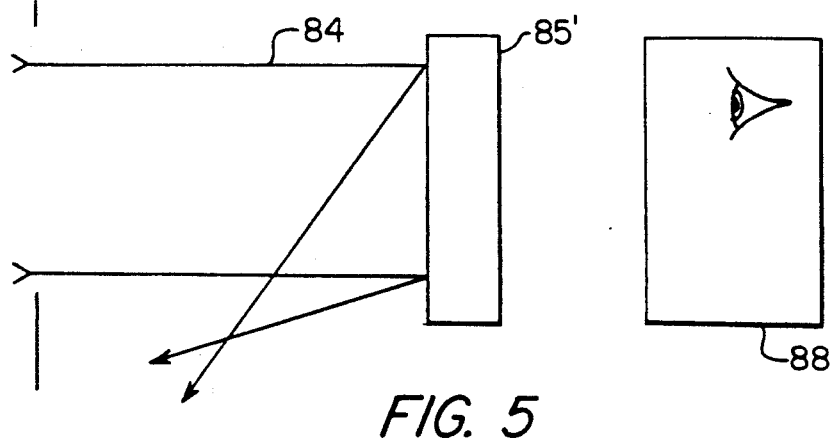
FIG. 5 is a schematic illustration indicating the reflection of a harmful laser beam from an in-line optical equipment or observer via refraction from a holographic optical element.

For a reflective HOE, as presented in FIG. 5, the laser beam 84 will be immediately pointed away from the system to be protected. There is no a priori need for an absorber, mirror, or baffle in this case.

It should be understood that the invention is not limited to the exact details of construction shown and described herein for obvious modifications will occur to persons skilled in the art.

We claim:

1. A method for protecting an observation point from a damaging beam of laser light comprising the steps:

simultaneously subjecting an exposed surface of a photographic film medium to reference and object coherent light beams, travelling in the same direction, for recording a holographic pattern thereon;

unidirectionally passing both reference and object light beams through the film medium, without reflection of light back therethrough;

photographically developing the pattern to form a holographic optical element;

positioning the optical element in line with the observation point;

subjecting the element to a damaging laser light beam; and deflecting the beam away from the observation point while concurrently allowing other ambient light to pass therethrough; and absorbing the deflected beam in a space adjacent the observation point.

2. A method for protecting an observation point from a damaging beam of laser light comprising the steps:

simultaneously subjecting an exposed surface of a photographic film medium to reference and object coherent light beams, travelling in the same direction, for recording a holographic pattern thereon;

unidirectionally passing both reference and object light beams through the film medium, without reflection of light back therethrough;

photographically developing the pattern to form a holographic optical element;

positioning the optical element in line with the observation point;

subjecting the element to a damaging laser light beam; and deflecting the beam away from the observation point while concurrently allowing other ambient light to pass therethrough; and reflecting the deflected beam in a space adjacent the observation point thereby further removing it from the observation point.

3. A method for protecting an observation point from a damaging beam of laser light comprising the steps:

simultaneously subjecting an exposed surface of a photographic film medium to reference and object coherent light beams, travelling in the same direction, for recording a holographic pattern thereon;

unidirectionally passing both reference and object light beams through the film medium, without reflection of light back therethrough;

photographically developing the pattern to form a holographic optical element;

positioning the optical element in line with the observation point;

subjecting the element to a damaging laser light beam; and deflecting the beam away from the observation point while concurrently allowing other ambient light to pass therethrough; and subjecting the deflected beam to an optical baffle in a space adjacent the observation point thereby shielding it from the observation point.

* * * * *